United States Patent [19]

Hahn et al.

[11] 4,093,864

[45] June 6, 1978

[54] PRIMARY X-RAY DIAPHRAGM ASSEMBLY

[75] Inventors: Alfred Hahn; Ernst Steiner; Rudolf Pospischil, all of Erlangen, Germany

[73] Assignee: Siemens Aktiengesellschaft, Berlin & Munich, Germany

[21] Appl. No.: 723,067

[22] Filed: Sep. 14, 1976

[30] Foreign Application Priority Data

Apr. 8, 1976 Germany .............................. 2615335

[51] Int. Cl.² .......................................... G03B 41/16
[52] U.S. Cl. .................................... 250/505; 250/511
[58] Field of Search ................. 250/505, 511, 512, 513

[56] References Cited

U.S. PATENT DOCUMENTS

| | | | |
|---|---|---|---|
| 2,542,196 | 2/1951 | Haupt | 250/513 |
| 3,546,463 | 12/1970 | Fekete | 250/511 |

*Primary Examiner*—Craig E. Church
*Attorney, Agent, or Firm*—Hill, Gross, Simpson, Van Santen, Steadman, Chiara & Simpson

[57] ABSTRACT

In the illustrated embodiments, a pair of primary X-ray diaphragm plates have cooperating front edges each with angled sections forming a generally V-shaped edge configuration and providing an included aperture angle facing the symmetry axis, of from 50° to 150°, the angled sections being connected by a definitely rounded central section for conforming to rounded boundary contours of different organs such as the heart. The diaphragm plates are advantageously oppositely inclined and crossed so as to be capable of assuming a symmetrical overlapping relation in defining small diaphragm apertures. Further the diaphragm plate front edges may exhibit progressively reduced absorption values to provide a penumbra effect about the freely transmitted cone of rays particularly so as to facilitate examination of marginal zones of an organ which is surrounded by regions of greatly reduced absorption value.

Motorized drive mechanism are illustrated for selectively translating the individual diaphragm plates toward and away from the symmetry axis and for jointly rotating the diaphragm plates. In a further development, a single motor speed selectively provides a relatively rapid rate of joint rotation of the plates and a substantially reduced rate of translational adjustment.

16 Claims, 5 Drawing Figures

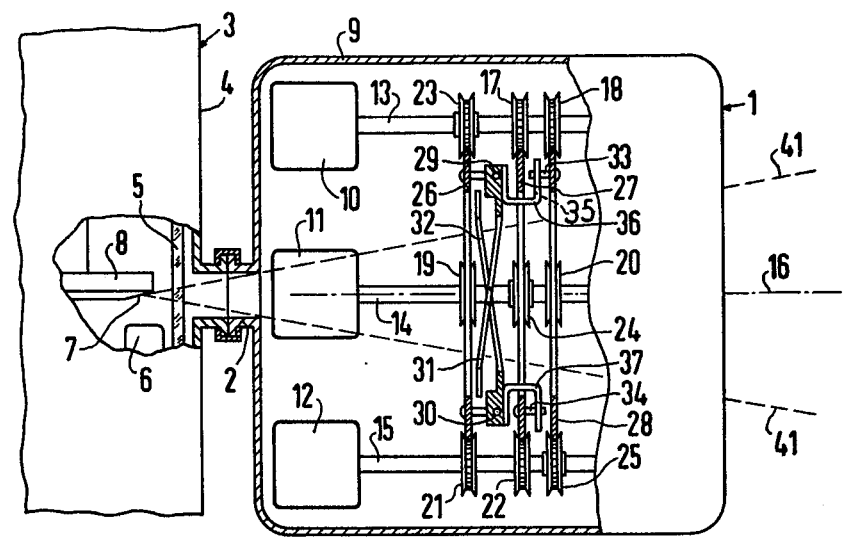
Fig.1
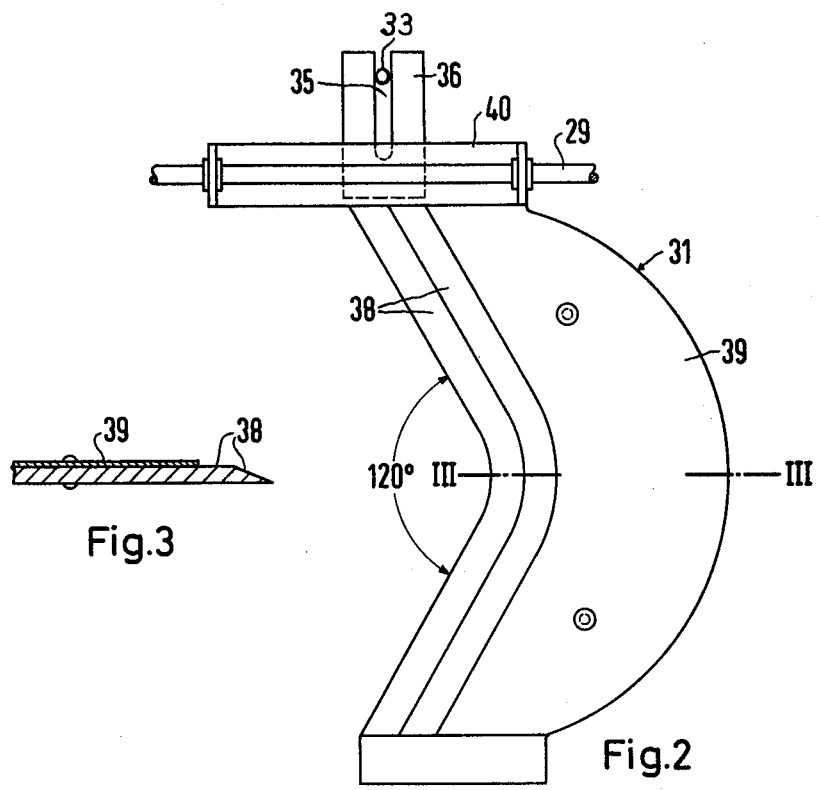
Fig.3
Fig.2

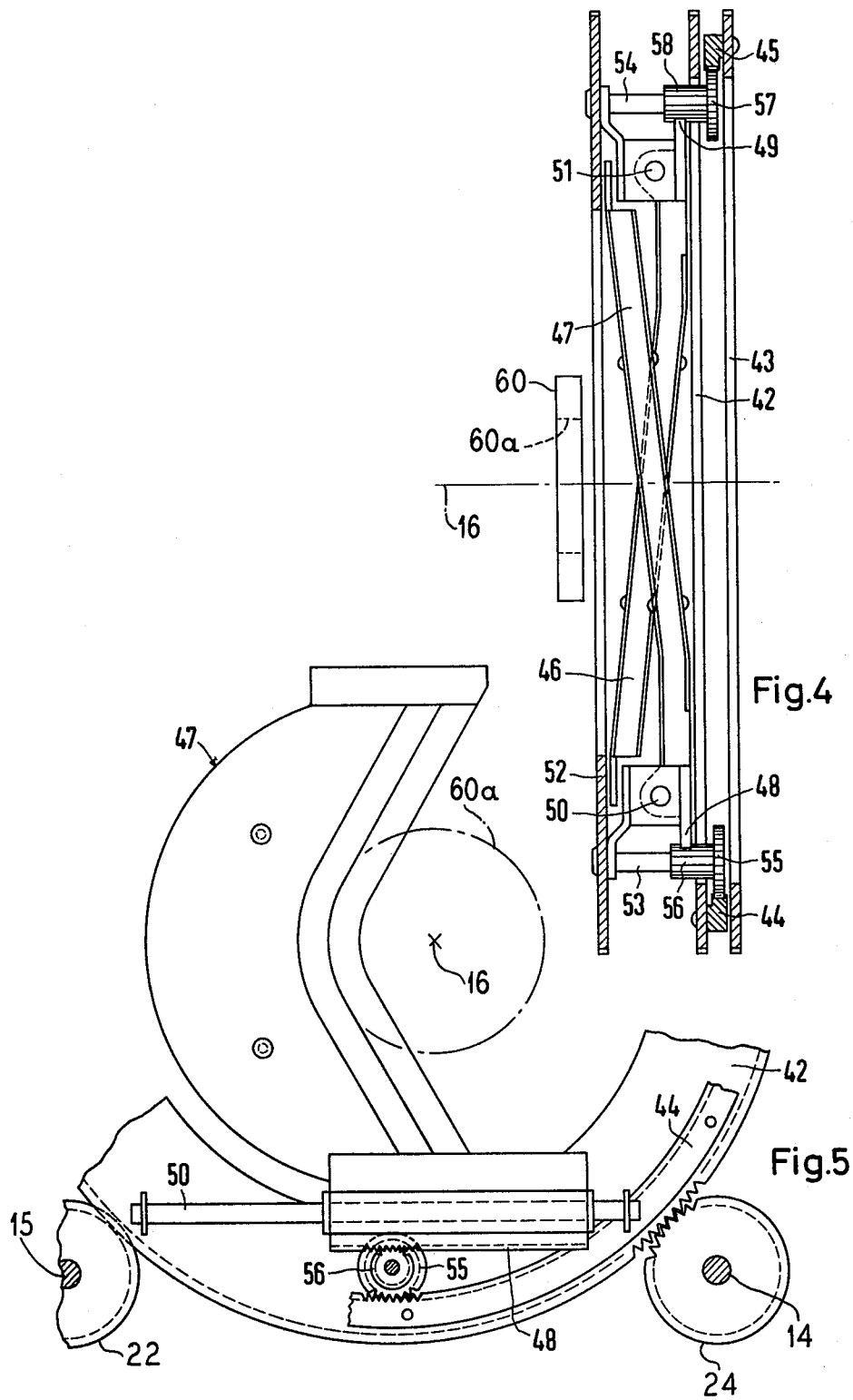

PRIMARY X-RAY DIAPHRAGM ASSEMBLY

BACKGROUND OF THE INVENTION

The invention relates to a primary X-ray diaphragm for an X-ray examination apparatus, with a plurality of diaphragm plates which define the cone of rays, the diaphragm plates being adjustable in a direction perpendicular to the symmetry axis of the primary X-ray diaphragm and being rotatable about the symmetry axis.

A primary X-ray diaphragm of the type referred in the preceding paragraph is already obvious from U.S. Letters Patent No. 3,287,561. With such a primary X-ray diaphragm, a rectangular or a square cone of rays can be delineated. Depending on need, the diaphragm can be rotated about the symmetry axis which most often coincides with the central ray from the X-ray tube to correspondingly rotate the cross section of the transmitted cone of radiation. A primary X-ray diaphragm with a rectangular diaphragm aperture which can be rotated about the symmetry axis meets the requirements of being able to completely utilize a cassette format or a film format, and to selectively adapt to either format. However, particularly in the examination of organs which border directly on regions of the body having a strongly reduced ray absorption, a disadvantage arises with respect to this primary X-ray diaphragm as a consequence of the rounded boundary contours of the organ which are to be recorded near the corners of a rectangular image format; in particular the radiation which passes laterally of the boundary contours of the organ to be examined and strikes the film, is only slightly attentuated as it passes through the adjoining body regions and thus over exposes the areas of the film corresponding to the boundary regions of the organ under examination. The consequence of this is that the recognizability of details in the areas of the film corresponding to such boundary regions is impaired. A typical example of this is in heart examinations where the coronary vessels are obscured as a result of the radiation which passes laterally adjacent to the heart and which is only slightly attenuated by the lung tissue.

From U.S. Letters Patent No. 3,631,249, it is obvious to delineate a circular diaphragm aperture in the case of primary X-ray diaphragms. These diaphragms serve the purpose of adjusting the cone of rays in conformity to the likewise-circular entry window of an X-ray image intensifier. These diaphragms of themselves do not admit of any other aperture cross section.

SUMMARY OF THE INVENTION

The problem which is the basis of the present invention is to construct a primary X-ray diaphragm which is adaptable, at least in aperture area, to body organs whose contours exhibit different radii. This diaphragm should be suitable particularly for heart examinations where there are particularly pronounced conditions, as a consequence of the mobility of the heart and the greatly differing absorption values of the heart muscle and the surrounding lung tissue.

Therefore, in the case of a primary X-ray diaphragm of the type referred to above, the invention specifies that the front edges of two plates (which define the cone of rays) are to be adjustable relative to one another via a motorized drive mechanism and are to have angled edge sections such that each edge as viewed in an aperture plane perpendicular to the direction of the central ray has a generally V shape which opens in a direction toward the symmetry axis of the diaphragm, the angled edge sections of each diaphragm plate having an aperture angle in a range from about 50° to about 150° as viewed in said aperture plane and having therebetween a definitely rounded central section to accommodate distinctly rounded boundary contours such as presented by the heart boundary regions. The advantage connected herewith is that these diaphragm plates can conform to different contours of the organs in the manner of a curved template. In addition, with the aid of two diaphragm plates, a comparatively good enclosure of the entire heart muscle can be achieved in the case of heart examinations.

In a particularly advantageous further development of the invention, both diaphragm plates can be inclined on a common transverse axis which is aligned parallel to the direction of adjustment of the diaphragm plates and which intersects the symmetry axis, the diaphragm plates being inclined in opposite directions relative to an intermediate plane which is oriented perpendicularly to the symmetry axis and each forming an angle of approximately 5° to 15° as compared with such intermediate plane. Where the symmetry axis of the primary X-ray diaphragm coincides with the central ray from the X-ray source, the intermediate plane between the planes of said diaphragm plates will coincide with the aperture plane previously mentioned. With the diaphragm plates inclined at opposite angles to an intermediate plane as just described, the diaphragm plates can be completely closed, and in the case of small diaphragm openings, the plates move virtually in one single plane, namely such intermediate plane.

The range of application of the primary X-ray diaphragm can be significantly expanded if the diaphragm plates, in an embodiment of the invention, have a reduced absorption value corresponding to an aluminum plate with a thickness in a range from about 0.5 to 35 mm so as to provide a penumbra effect about the main cone of rays transmitted by the diaphragm aperture. The marginal zones of the organ covered by the diaphragm plates thereby nevertheless remain visible on the fluoroscopic screen or X-ray film, even in the case of less exact adaptation of the diaphragm front edges to the boundary contours of the organ under examination.

Other objects, features and advantages of the invention will be apparent from the following detailed description taken in connection with the accompanying sheets of drawings showing two exemplary embodiments.

BRIEF DESCRIPTION OF THE DRAWINGS

FIG. 1 shows a diagrammatic side elevational view of a primary X-ray diaphragm assembly according to the present invention associated with an X-ray apparatus by means of mating flanged fittings, with portions of the housing of the diaphragm and of the X-ray apparatus being broken away and interior parts being diagrammatically indicated;

FIG. 2 shows an enlarged view of one of the diaphragm plates of the primary X-ray diaphragm of FIG. 1 together with a portion of a guide means for mounting such diaphragm plate;

FIG. 3 illustrates a partial sectional view taken generally along the line III—III of FIG. 2;

FIG. 4 illustrates a modified regulating drive mechanism for a primary X-ray diaphragm assembly in accordance with the present invention; and FIG. 5 is a partial somewhat diagrammatic illustration of the regulating drive mechanism for one of the diaphragm plates of FIG. 4 as viewed from the X-ray source.

DETAILED DESCRIPTION

In FIG. 1 a primary X-ray diaphragm assembly 1 is shown which is secured to an X-ray source 3 by means of a flange-like fitting 2. In the interior of the protective housing 4 of X-ray source 3, a portion of a glass wall 5 of the X-ray tube envelope is indicated as containing a cathode 6 for emitting electrons so as to converge to a focus at a region 7 of the path of a rotating anode plate 8. The housing 9 of the primary X-ray diaphragm 1 is shown as containing three electric motors which in an actual embodiment may be mounted equally distant from a central longitudinal axis of housing 9 and may be mounted on the end wall of the housing which is adjacent to the X-ray source 3. The motors 10, 11 and 12 are shown as having respective motor shafts 13, 14 and 15 which are oriented parallel to the central axis of the housing 9 which in the illustrated embodiment coincides with the symmetry axis 16 of the primary X-ray diaphragm 1 and with the central ray of the X-ray energy which is being transmitted through the housing 9. A plurality of free-running idler gears 17, 18, 19, 20, 21, 22 are mounted on the shafts of the electric motors, as well as respective drive gears 23, 24, 25, each of which is rigidly pinned to its associated shaft. Between these gears, three rim gears 26, 27, 28 of flat annular configuration are rotatably supported so as to be symmetrical about symmetry axis 16, the planes of the respective rim gears each having an orientation which is perpendicular to the symmetry axis 16. On a first rim gear 26, which is shown closest to the X-ray source 3, guides 29, 30 are mounted parallel relative to one another and on opposite sides of the symmetry axis 16. The guides 29, 30 carry respective diaphragm plates 31, 32 for adjustment parallel to an intermediate plane which is intermediate the diaphragm plates 31 and 32 and perpendicular to the symmetry axis 16. Second and third rim gears 27, 28 are provided at their circumference with respective driver means in the form of pins 33, 34, respectively, each of which is aligned parallel to the symmetry axis 16 of the diaphragm. The pins 33, 34 each slidably engage in a longitudinal slot such as slot 35, FIG. 2, of respective carrier stirrups 36, 37 which are secured to the respective diaphragm plates 31, 32 as shown in FIG. 1.

An individual diaphragm plate 31 is shown in FIG. 2. In FIG. 3, the so-called front edge of this diaphragm plate (which defines one side of the diaphragm aperture of the primary diaphragm) is illustrated in section. In FIG. 2 it is easily recognizable that this front edge 38 of diaphragm plate 31 has a V-shaped outline or edge configuration as viewed in the aperture plane perpendicular to the X-ray direction and in the illustrated embodiment coinciding with the drawing plane of FIG. 2. The aperture angle included between the angled sections of this "V" amounts to 120°, for example, as is indicated in FIG. 2. The inner or central portion of the "V" is strongly rounded so as to accommodate distinctly rounded boundary contours such as presented by the heart boundary regions, for example. The rounding of this central section has a radius of 35 mm in the exemplary embodiment. Radii of from about 25 to 40 mm provide usable solutions. As illustrated in the sectional view of FIG. 3, the front edge 38 (which defines a side of the radiation aperture) of diaphragm plate 31 has a wedge-shaped construction. At a distance from this edge 38 of from 1 to 2 cm additional plate 39 of iron is riveted onto the actual diaphragm plate 31 which is constructed from aluminum. This additional iron plate increases the absorption of X-ray energy. Even in this rear area, the composite diaphragm plate formed by aluminum plate 31 and iron plate 39 is still semi-permeable to the radiation used. On its one end, the diaphragm plate 31 is provided with a U-shaped metal sheet 40 with aligned bores in the legs for receiving the associated guide rod 29 as indicated in FIG. 2 so that the diaphragm plate 31 is mounted by rim gear 26 for translational adjustment toward and away from the symmetry axis 16. In addition, the carrier stirrup 36 may have one side thereof secured to the base of the U-shaped metal sheet 40 and may have an opposite side provided with the slot 35 for receiving the driver pin 33 as indicated in FIG. 1.

When the three illustrated electric motors 10, 11, 12 are switched simultaneously, the three rim gears 26, 27, 28 are rotated with the same velocity via gears 23, 24, 25, the shaft 13 driving rim gear 26 via gear 23, the shaft 14 driving rim gear 27 via gear 24 and the shaft 15 driving rim gear 28 via gear 25. What is achieved thereby is that the diaphragm plates 31, 32 rotate with an unchanged mutual spacing about the symmetry axis 16 of the primary X-ray diaphragm assembly 1. If, on the contrary, only electric motor 11 or 12 is energized, only the corresponding rim gear 27 or 28 is rotated, and in this case the associated driver pin 33 or 34 moves in an arcuate path about the symmetry axis 16. The driver pin 33 or 34 so activated moves the associated carrier stirrup 36 or 37 of the corresponding diaphragm plate 31 or 32, such diaphragm plate together with its U-shaped metal sheet, such as 40, being guided in its translational adjustment by means of the associated stationary guide rod 29 or 30. Depending upon the direction of rotation of the active electric motor, the associated diaphragm plate is moved toward or away from the symmetry axis 16. The consequence of this is that each individual one of the diaphragm plates 31, 32 can be individually adjusted, arbitrarily and independently of the other diaphragm plate, by activating the corresponding electric motor 11 or 12 while the motor 10 remains deenergized.

Since as the illustration of FIG. 1 shows, the planes of the diaphragm plates 31, 32 intersect along a common transverse axis which is aligned and parallel to the direction of adjustment of the diaphragm plates and which intersects the symmetry axis 16, both diaphragm plates can entirely close off the cone of rays 41 in spite of their V-shaped edge configurations such as shown at 38 in FIG. 2. In the case of very small aperture sizes of the primary X-ray diaphragm 1, what is also achieved is that the edges such as 38 (defining the cone of rays 41) of diaphragm plates 31, 32 are located virtually in one single plane, the rounded central sections of the edges such as 38, for example, being located substantially in a common intermediate plane coinciding with the common transverse axis and disposed perpendicularly to the symmetry axis 16. This leads to an excellent symmetry in the area of the marginal zones about the cone of rays which has been diaphragmed out or defined by the diaphragm aperture.

The V-shaped form of the edges such as 38 of the diaphragm plates 31, 32 facilitates the adaption of the cone of transmitted rays to the contours of organs or seats of disease. This is particularly advantageous if these organs are in an environment whose absorption coefficient is much less than that of the organ which is to be examined. Thus, in the examination of the heart, for example, those portions of the radiation which pass laterally of the heart and impinge on the film are much stronger in their intensity. They thereby relatively overexpose the marginal zones of the actual area under examination. Due to the shape of the edges such as 38 defining the transmitted radiation, this peripheral radiation adjoining the area of interest can be masked or attenuated in a significantly improved fashion. As a consequence of the markedly reduced absorption value of the edges such as 38 of the diaphragm plates 31, 32, a penumbra formation is achieved adjoining the main cone of rays. Because of the gradually increasing absorption values provided by the diaphragm plates 31, 32 with respect to the direction from the inner margins of edges such as 38 to the iron plates such as 39, the radiation passing laterally of the organ is progressively weakened as a function of increasing distance from the main cone of rays to such an extent, even in the case of only an approximate adaptation of the main cone of rays to the contour of the organ, that a relative over-exposure with respect to the peripheral portions of the organ is avoided.

FIGS. 4 and 5 show a modification of the regulating drive mechanism for the two diaphragm plates. This modification differs from the embodiment as shown in FIGS. 1 and 2 in that, instead of the driver pins 33, 34, FIG. 1, arcuate gear segments 44, 45 with internal gear teeth are mounted on the second and third rim gears designated by reference numerals 42 and 43 in FIG. 4. Instead of the U-shaped carrier stirrups 36, 37 of FIG. 1, linear racks 48, 49 are mounted on the respective diaphragm plates 46, 47, the rack 48 being diagrammatically indicated in side elevation in FIG. 5. In addition, as FIG. 4 makes clearly recognizable, shafts 53, 54 are mounted on the first rim gear 52 which also carries the guides 50, 51 for guiding the translational movement of the respective diaphragm plates 46, 47. The shafts 53, 54 are shown as being mounted radially outwardly of the guides 50, 51, respectively. On each of the shafts 53, 54, pairs of pinions 55, 56 and 57, 58, respectively, are mounted in a freely rotatable fashion, the pinions 55 and 56 being secured together for joint rotation and having different diameters so as to provide a speed reduction between the tangential velocity of the arcuate gear segment 44, FIG. 5, and the linear movement of the rack 48. Similarly, the pinions 57 and 58 are secured together for joint rotation and have different diameters to provide a corresponding speed reduction in the translational adjustment of the diaphragm plate 46. The drive mechanism of FIGS. 4 and 5 is such that the relative translational displacement of the diaphragm plates 46, 47 can take place with a reduced speed differing greatly from the speed of translational adjustment provided in the embodiment of FIGS. 1 and 2 for a given rotational rate of the rim gears. Furthermore, with the embodiment of FIGS. 4 and 5, such reduced speed of translational adjustment in relation to a given rate of diaphragm aperture rotation is achieved without having to operate the electric motors such as 10, 11, 12 at a different speed for the joint rotation of the three rim gears in comparison to the individual operating speed of motor 11 or 12 for effecting individual translational adjustment of one of the diaphragm plates.

Diaphragm plates such as 31, 32, and 46, 47 having a V-shaped angulation such as indicated for edge 38 in FIG. 2 have been proven especially expedient not only in the case of heart examinations, but in all those cases in which organs are to be examined which are adjacent to areas of the body having a strongly reduced X-ray absorption. In this category are included not only areas of the body with different specific absorptions values, such as lung tissues and muscle tissues, but also areas of the body having a different density such as at exterior surfaces of the body, for example. Thus, the recognizability of details, for example in the case of kidney angiography, in the case of examinations in the spleen or the liver region, as well as in the case of investigations of the bladder and the esophagus passage, could be clearly improved. Due to the semi-transparent construction of the diaphragm plates, even overlappings of the contours of the diaphragm plates with the respective organ peripheries are tolerable if there is a corresponding stronger concentration of rays. In the case of a combination of the V-shaped diaphragm plates with an iris diaphragm which is already known per se in the art, the iris diaphragm may be installed in the diaphragm housing 1 in advance of the first rim gear and may have a semi-transparent construction. Such iris diaphragm of semi-transparent construction can overlap the central regions of the primary diaphragm edges such as 38 so as to vary the cross section of the cone of rays by means of superposition in comparison to the radius of curvature provided by the rounded central portions of the V-shaped primary diaphragm plate edges such as 38.

By way of supplemental discussion, it will be noted that while FIG. 5 may be taken as illustrating motor shafts such as 14 and 15 with respectively a drive gear 24 and an idler gear 22, it will be apparent that a normal arrangement would space the successive shafts equally about the perimeter of the rim gears so that shafts 14 and 15 as shown in FIG. 5 would have an angular separation of 120° in an actual embodiment. Details of the mounting of rods 50 and 51 have been indicated in FIGS. 4 and 5, and similar mounting means may, of course, be provided for the rods 29 and 30 in FIGS. 1 and 2. It will be observed from FIGS. 1 and 4 that the two cooperating diaphragm plates such as 31, 32 and 46, 47 may be of identical construction in the illustrated embodiments with identical edge configurations corresponding to that described for edge 38 in FIG. 2, in each case the radiation absorption progressively increasing because of the wedge configuration of the margin of edge 38 and because of the superimposed iron plate 39 inwardly of the edge 38. In each of the illustrated embodiments, the intermediate plane such as represented by the plane of FIG. 2 or FIG. 5 and lying at right angles to the symmetry axis 16 may be symmetrically disposed between the respective pairs of diaphragm plates 31, 32 and 46, 47 such that each plate forms an angle of from approximately 5° to approximately 15°. As is generally indicated in FIG. 1, all of the parts of the drive mechanism for the diaphragm plates, in an actual construction, would be clear of the maximum cross section cone of rays such as indicated at 41 at FIG. 1.

For the sake of an exemplary showing, an iris diaphragm has been indicated at 60 in FIG. 4 and an exemplary aperture size has been indicated by dot-dash circle 60a in FIG. 5. Such diaphragm 60 may be of aluminum of a thickness to be semi-transparent to X-ray energy as herein explained. Accordingly the curved cross sectional configuration of the overall effective diaphragm aperture can be provided with different rounded segments than those provided by the central parts of V- shaped edge configurations such as shown at 38 in FIG. 2 by superimposing the attenuations introduced by the iris diaphragm 60 and the diaphragm plates 31, 32 or 46, 47.

The diaphragm assemblies shown herein are termed "primary" since they are interposed between the X-ray source and the patient. The term "cone of rays" is used to refer to the beam of X-ray energy as it is emitted from the X-ray source or from the primary diaphragm assembly. The term "absorption value" is used to describe the degree of absorption of the X-ray energy by the interposed solid material under discussion. The term "central ray" is used to refer to the X-ray energy being propagated along the central longitudinal axis of the cone of X-rays (such as 41, FIG. 1) and the direction of transmission of the X-ray energy is taken as being along such central ray.

As shown in FIGS. 1 and 4, the diaphragm plates are preferably arranged in a symmetrical crossed relationship as viewed in the plane of FIG. 1 or FIG. 4 and this symmetrical crossed arrangement may be maintained as the oppositely directed generally V-shaped edge configurations are moved toward each other into a progressively more completely overlapping interfitting relationship.

While there have been disclosed exemplary embodiments representing presently preferred practice of the claimed invention, it will be apparent that many modifications and variations may be effected without departing from the scope of the novel teachings and concepts of the present invention.

We claim as our invention:

1. In a primary X-ray diaphragm assembly for X-ray examination apparatus, including a plurality of diaphragm plates which define a cone of rays, said diaphragm plates being adjustable in a direction generally perpendicular to a symmetry axis of the diaphragm plates and being rotatable about the symmetry axis, said diaphragm plates having cooperating front edges for defining a diaphragm aperture with respect to an aperture plane perpendicular to the direction of transmission of X-ray energy in said cone of rays, said front edges of said diaphragm plates being of X-ray absorbing material for relatively attenuating the transmission of X-ray energy impinging on said edges in comparison to the cone of rays transmitted by such diaphragm aperture, and motorized drive mechanism coupled with said diaphragm plates for adjusting said diaphragm plates relative to one another to vary the size of said diaphragm aperture, said edges of said diaphragm plates including angularly related edge sections and central edge sections defining oppositely directed generally V-shaped edge configurations as viewed in said aperture plane with the V-shaped edge configurations opening toward the symmetry axis, the angularly related edge sections of each V-shaped edge configuration having an angle therebetween in the range from about 50° to about 150°, and the central edge section of each V-shaped edge configuration being rounded for defining diaphragm apertures accommodating distinctly rounded contours, said motorized drive mechanism having means for selectively individually adjusting one only of the respective diaphragm plates while the other diaphragm plate remains stationary.

2. A primary X-ray diaphragm assembly according to claim 1 with two diaphragm plates having respective front edges defining the respective generally V-shaped edge configurations as viewed in said aperture plane, said front edges of said two diaphragm plates being inclined in opposite directions in a symmetrical crossed relationship such that the front edges can progressively overlap while symmetry is maintained as the aperture size is progressively reduced.

3. A primary X-ray diaphragm assembly according to claim 1 with the front edges of two diaphragm plates defining the respective V-shaped edge configurations as viewed in said aperture plane, the diaphragm plates being inclined relative to a common transverse axis which is aligned parallel to the direction of adjustment of the diaphragm plates toward and away from one another, the planes of said diaphragm plates being oppositely inclined as compared with an intermediate plane which is oriented perpendicularly to the symmetry axis and each forming an angle of approximately 5° to 15° as compared with such intermediate plane.

4. A primary X-ray diaphragm assembly according to claim 1 with said front edges of said diaphragm plates having a reduced absorption value in comparison to other portions of said diaphragm plates so as to define a penumbra region about the cone of rays transmitted by the diaphragm aperture.

5. A primary X-ray diaphragm assembly according to claim 1 with said front edges of said diaphragm plates having an absorption value corresponding to that of a thickness of from about 5/10 millimeter to about 35 millimeters of aluminum.

6. A primary X-ray diaphragm assembly according to claim 5 with said front edges of said diaphragm plates having progressively decreasing absorption values in the direction toward the symmetry axis so as to define a penumbra region of progressively decreasing intensity outwardly of the cone of rays transmitted by the diaphragm aperture.

7. A primary X-ray diaphragm assembly according to claim 5 with said front edges of said diaphragm plates having a wedge-shaped cross section.

8. A primary X-ray diaphragm assembly according to claim 1 with said drive mechanism comprising rim gears disposed for rotation in respective parallel planes perpendicular to the symmetry axis and each being generally symmetrical about the symmetry axis, motor means for independently rotating the respective rim gears, respective guide means disposed parallel to the planes of such rim gears for mounting the respective diaphragm plates for translation thereon, the rim gears having respective driver means coupled with the respective diaphragm plates, and said motor means being operative to selectively rotate said rim gears so as to selectively adjust the respective diaphragm plates along their respective guide means.

9. A primary X-ray diaphragm assembly according to claim 8 with said motor means comprising respective individual electric motors for rotating the respective rim gears.

10. A primary X-ray diaphragm assembly according to claim 9 with said electric motors having respective motor shafts extending parallel to the symmetry axis of the diaphragm plates and being angularly spaced about the circumference of the rim gears and the motor shafts carrying respective drive gears for driving the respective rim gears and carrying idler pinions for guiding the rotation of the other of said rim gears.

11. A primary X-ray diaphragm assembly according to claim 1 with said drive mechanism comprising three rim gears disposed for rotation in respective parallel planes perpendicular to the symmetry axis and each being generally symmetrical about the symmetry axis, motor means for rotating a first of said rim gears jointly with second and third ones of said rim gears and for individually rotating each of the second and third rim gears, the first rim gear having respective guide means mounted thereon and disposed parallel to the planes of said rim gears for mounting the respective diaphragm plates for translation therealong, and the second and third rim gears having respective driver means coupled with the respective diaphragm plates so as to selectively adjust the respective diaphragm plates along their respective guide means in response to selective individual rotation of said second and third rim gears by means of said motor means.

12. A primary X-ray diaphragm assembly according to claim 1 with said drive mechanism comprising motor means having a drive coupling with said diaphragm plates so as to produce joint rotation thereof at a rotational rate corresponding to a given tangential velocity of the margins of said diaphragm plates remote from said symmetry axis, and having a speed reduction coupling with the individual diaphragm plates for individually translating said diaphragm plates toward and away from said symmetry axis at a reduced linear velocity in comparison to said tangential velocity while said motor means operates at a fixed rate corresponding to said rotational rate.

13. A primary X-ray diaphragm assembly according to claim 8 with said drive mechanism for translational adjustment of said diaphragm plates comprising respective linear racks disposed parallel to said guide means and secured to the respective diaphragm plates, respective pinion means mounted in driving relation to the respective linear racks, and the driver means comprising an arcuate gear segment on each of said rim gears for transmitting the rotational movement thereof at a rotational rate corresponding to a given tangential velocity of such gear segment to a linear translational velocity of the associated rack and diaphragm plate which is substantially reduced in comparison to said given tangential velocity.

14. A primary X-ray diaphragm assembly according to claim 11 with said drive mechanism for translational adjustment of said diaphragm plates comprising respective linear racks disposed parallel to said guide means and secured to said diaphragm plates, respective pinion means freely rotatably mounted on said first rim gear in meshing relation to the respective linear racks, and the driver means comprising an arcuate gear segment on each of said rim gears with internal gear teeth for transmitting the rotational movement of said first and second rim gears at a rotational rate corresponding to a given tangential velocity of said gear teeth to a linear translational velocity of the associated rack and diaphragm plate, said pinion means each comprising a larger diameter pinion meshing with the interior gear teeth of the associated arcuate gear segment and a smaller diameter pinion meshing with the associated linear rack in order to reduce the translational adjustment speed of the diaphragm plates in comparison to said given tangential velocity.

15. A primary X-ray diaphragm assembly according to claim 1 with an iris diaphragm along the path of the cone of rays defined by said diaphragm aperture and operable for further attenuating portions of said cone rays so as to further adapt the cone of rays to distinctly rounded contours.

16. A primary X-ray diaphragm assembly according to claim 1 with two diaphragm plates having respective front edges defining the respective generally V-shaped edge configurations as viewed in said aperture plane, said front edges of said two diaphragm plates being inclined in opposite directions in a symmetrical crossed relationship such that the front edges can progressively overlap while symmetry is maintained as the aperture size is progressively reduced, and said diaphragm plates being movable toward each other to a completely closed relationship to entirely close off the diaphragm aperture.

* * * * *